US00PP31351P2

(12) United States Plant Patent
Eveleens

(10) Patent No.: US PP31,351 P2
(45) Date of Patent: Jan. 14, 2020

(54) ***HYDRANGEA* PLANT NAMED 'HORTHAT'**

(50) Latin Name: *Hydrangea macrophylla*
Varietal Denomination: Horthat

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Baskoop (NL), part interest ( * ) Notice: Subject to any disclaimer, the term of this patent is extended or adjusted under 35 U.S.C. 154(b) by 0 days.

(21) Appl. No.: 15/999,956

(22) Filed: Aug. 30, 2018

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ... A01H 5/02; A01H 5/00; A01H 1/02; A01H 6/48; A01H 6/00
See application file for complete search history.

(56) References Cited

PUBLICATIONS

Berger Garden Design Online New Plants 2018, retrieved on Jun. 12, 2019, retrieved from the Internet at https://www.gardendesignonline.com/gardendesignonline/2018/01/new-plants-2018-i.html, one page. (Year: 2018).*

Plants Nouveau, retrieved on Jun. 13, 2019, retrieved from the Internet at http://plantsnouveau.com/plant/hydrangea-seaside-serenade-hatteras/, 2pp. (Year: 2019).*

* cited by examiner

*Primary Examiner* — June Hwu
(74) *Attorney, Agent, or Firm* — Penny J. Aguirre

(57) ABSTRACT

A new cultivar of *Hydrangea macrophylla* plant named 'Horthat' that is characterized by its compact plant habit, its mophead inflorescences that are dark rose in color, its sturdy and thick textured flowers, its inflorescences that are relatively small in size and globular in shape, and its suitability as a potted plant.

2 Drawing Sheets

Botanical classification: *Hydrangea macrophylla.*
Varietal denomination: 'Horthat'.

CROSS REFERENCE TO RELATED APPLICATIONS

This application is co-pending with a U.S. Plant Patent Application filed for a plant derived from the same breeding program that are entitled *Hydrangea* Plant Named 'Hortmavi' (U.S. Plant patent application Ser. No. 15/999,948) and 'Hortmagitri' (U.S. Plant Pat. No. 30,044).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings on Monrovia.com and plantsnouveau.com.

BACKGROUND OF THE INVENTION

The present invention relates to a new and distinct cultivar of *Hydrangea macrophylla* and will be referred to hereafter by its cultivar name, 'Horthat'. 'Horthat' represents a new bigleaf *Hydrangea*, a perennial shrub grown for landscape use and as a potted plant.

'Horthat' derived from an ongoing controlled breeding program directed by the Inventor. An objective of the breeding program included developing a new cultivar of *Hydrangea* with flowers that are dark rose in color combined with other desirable straits.

'Horthat' arose from a controlled cross made by the Inventor in Boskoop, The Netherlands in May of 2009 between unnamed and unpatented proprietary plants in the Inventor's breeding program; reference no. 08-007-02 as the female parent and reference no. 08-016-02 as the male parent. 'Horthat' was selected as a single unique plant from amongst the resulting seedlings in August of 2016.

Asexual propagation of the new cultivar was first accomplished by stem cuttings by the Inventor in Boskoop, The Netherlands in August of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Horthat' as a unique cultivar of *Hydrangea macrophylla.*

1. 'Horthat' exhibits a compact plant habit.
2. 'Horthat' exhibits mophead inflorescences that are dark rose in color.

3. 'Horthat' exhibits sturdy and thick textured flowers.
4. 'Horthat' exhibits inflorescences that are relatively small in size and globular in shape.
5. 'Horthat' exhibits suitability as a potted plant.

The female parent of 'Horthat' differs from 'Horthat' in have fewer flowers, a slightly lighter inflorescence color and fewer branches. The male parent of 'Horthat' differs from 'Horthat' in having fewer flowers and fewer branches. 'Horthat' can be most closely compared to the *Hydrangea macrophylla* cultivars 'Kolmaru' (U.S. Pat. No. 25,104), 'Hortmagitri' and 'Hortmavi'. 'Kolmaru' is similar to 'Horthat' in being a mophead type *Hydrangea*. 'Kolmaru' differs from 'Horthat' in having flowers that are dark red in color, inflorescences that are larger in size and sterile flower sepals that are less sturdiness and thick. 'Hortmagitri' is similar to 'Horthat' in being a mophead type *Hydrangea* and in having sturdy, thick sterile flower sepals. 'Hortmagitri' differs from 'Horthat' in having flower color that is red with a flush of darker red. 'Hortmavi' is similar in plant habit and inflorescence shape, and in having sturdy sterile flower sepals. 'Hortmavi' differs in having larger inflorescences that are dark pink in color.

BRIEF DESCRIPTION OF THE DRAWINGS

The accompanying colored photographs illustrate the overall appearance and distinct characteristics of the new *Hydrangea*. The photographs were taken of a two-year-old plant of 'Hortmavi' as grown in a greenhouse in 3-gallon containers in Visalia, Calif.

The photograph in FIG. 1 provides a side view of the plant habit of 'Horthat' in bloom with inflorescences in various stages of development.

Figure 1:
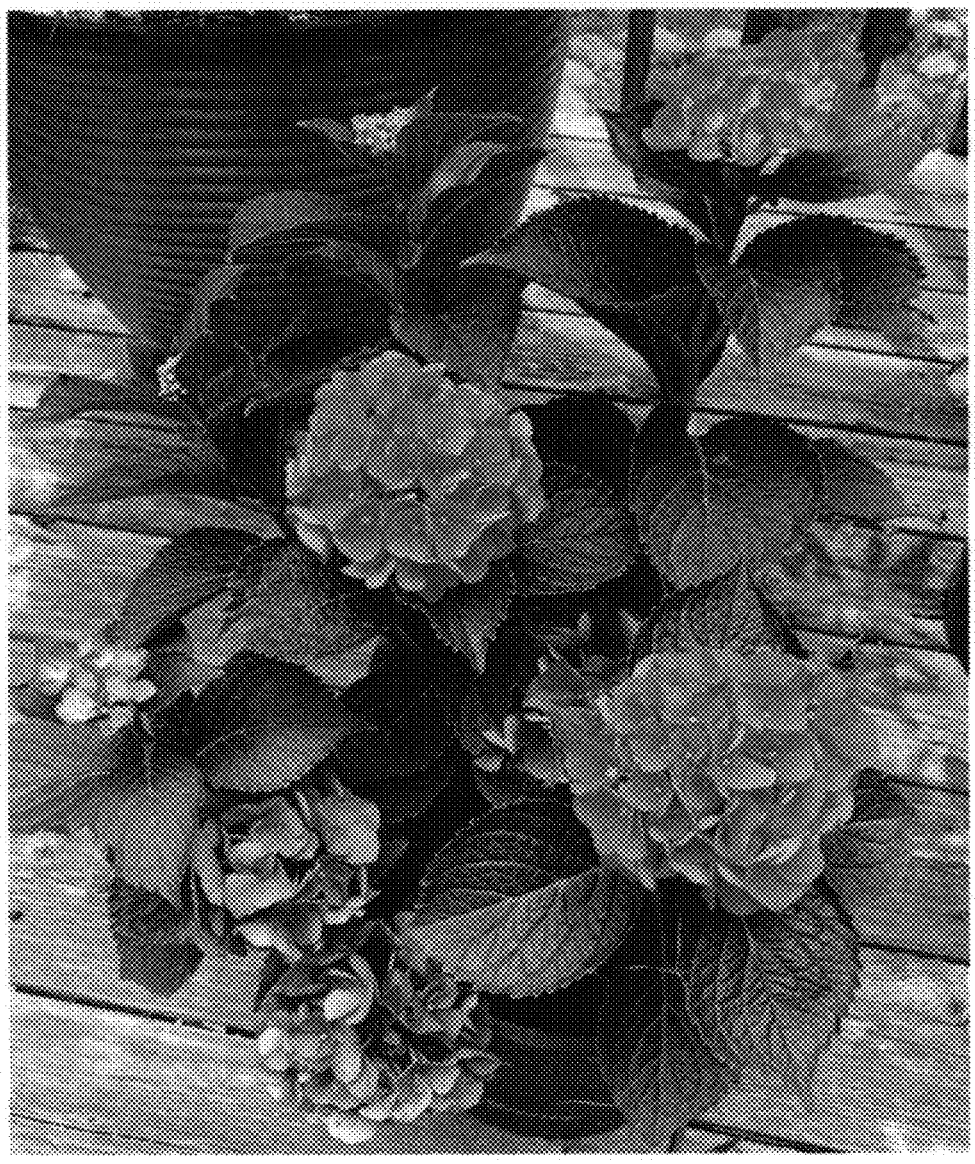
Figure 2:
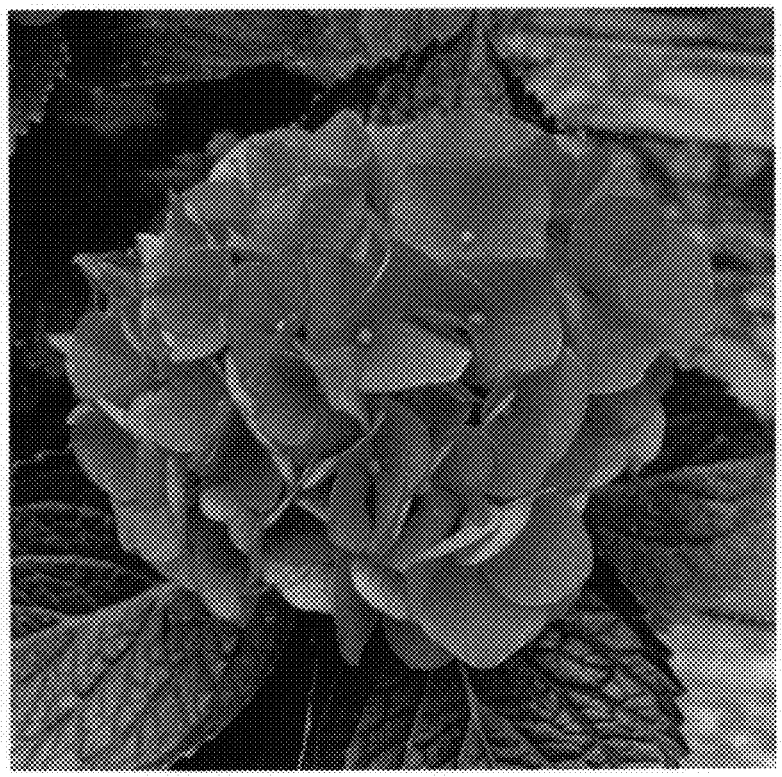

The photograph in FIG. 2 provides a close-up view of a fully open inflorescence of 'Horthat'.

Figure 3:
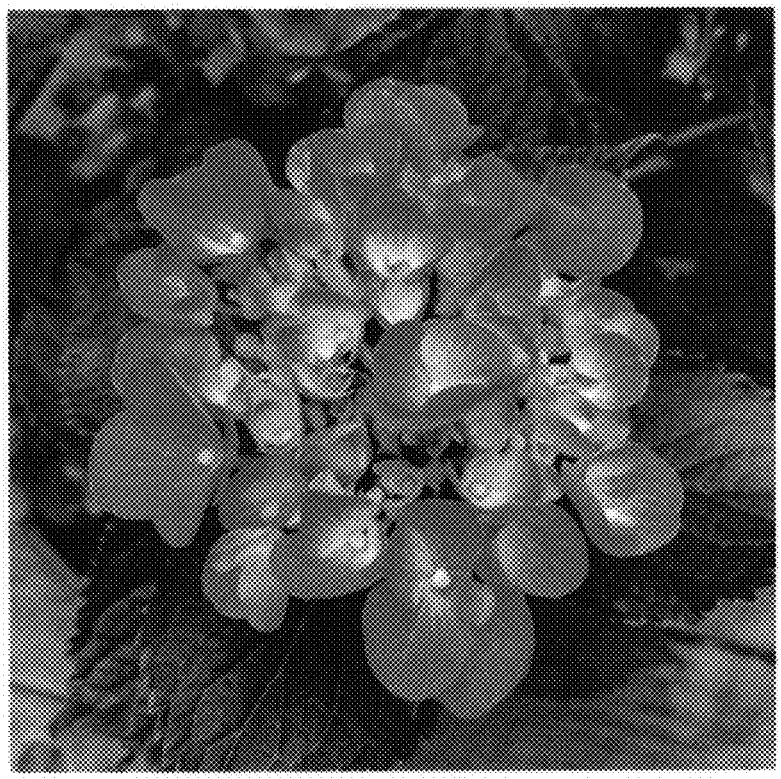

The photograph in FIG. 3 provides a close-up view an opening inflorescence of 'Horthat'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Hortmavi' as grown in a greenhouse in 3-gallon containers in Visalia, Calif. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—From May to July in a greenhouse and from July to September when grown outdoors in the Netherlands.

*Plant type.*—Deciduous shrub, mophead type *Hydrangea.*

*Plant habit.*—Broad upright, compact.

*Height and spread.*—An average of 37 cm in in height and 30 cm in spread as grown in a 3-gallon container, reaches 1 m in height and spread as a 3-year-old plant in the landscape.

*Hardiness.*—At least U.S.D.A. Zones 5 to 9.

*Diseases resistance.*—No susceptibility and resistance has been observed.

*Root description.*—Fine and fibrous, 161C in color.

*Propagation.*—Stem cuttings.

*Root development.*—An average of 3 weeks for root initiation with a young rooted plant produced in an average of six weeks.

*Growth rate and vigor.*—Moderate.

Stem description:

*Stem shape.*—Oval, no fasciation is present.

*Stem strength.*—Very strong.

*Stem color.*—Young and mature growth; 144A to 144B, woody bark; a blend of 161B and N199D.

*Stem size.*—An average of 24 cm in length and 4.5 mm in diameter.

*Stem surface.*—Glabrous and satiny, sparsely lenticellate, lenticels; 6 per stem cm in length, an average of 1.5 mm in length and 1 mm in width, 187A in color, bark; moderately rough with fissures.

*Stem aspect.*—Held primarily upright.

*Internode length.*—An average of 3.7 cm.

*Branching.*—Freely branching with an average of 11 lateral branches.

*Stipules.*—Ovate in shape, an average of 2 mm in length and 1.5 mm in width, apiculate apex, truncate base, glabrous surface, color 144A at base and 187A at apex.

Foliage description:

*Leaf shape.*—Elliptic to slightly ovate.

*Leaf arrangement.*—Opposite.

*Leaf division.*—Simple.

*Leaf base.*—Obtuse to broad cuneate.

*Leaf apex.*—Broad apiculate.

*Leaf margins.*—Serrate.

*Leaf venation.*—Pinnate, color; color upper surface 146C to 146D and lower surface 146C and 146D blending into 138B towards the outer portion of leaf blade.

*Leaf size.*—An average of 9.5 cm in length and 6.3 cm in width.

*Leaf attachment.*—Petiolate.

*Leaf number.*—An average of 12 per lateral stem.

*Leaf surface.*—Both surfaces; glabrous and slightly rugose, young leaves satiny on upper surface and satiny on lower surface, mature leaves dull on both surfaces.

*Leaf color.*—Young foliage; upper surface 144A and blending to 137A at apex and lower surface 137C, mature foliage; upper surface a blend of 137A and NN137A, lower surface 138A.

*Petioles.*—An average of 1.2 cm in length and 4 mm in diameter, 144B in color, surface glabrous and satiny to glossy, flattened on upper surface and rounded on lower surface.

Inflorescence description:

*Inflorescence type.*—Terminal panicle, rounded mophead in form comprised of a sterile flowers above fertile flowers.

*Lastingness of inflorescence.*—Sterile flowers; persistent for an average of 5 weeks, fertile flowers; an average of 5 days, self-cleaning.

*Inflorescence number.*—One per lateral stem.

*Inflorescence size.*—An average of 7 cm in height and 10 cm in diameter.

*Flower number.*—An average of 48 sterile flowers and 15 fertile flowers per panicle.

*Flower fragrance.*—None.

*Flower aspect.*—Upright to stem.

*Flower size.*—Sterile flowers; an average of 3.5 cm in diameter and 1.3 cm in depth, fertile flowers; an average of 7 mm in diameter and 4 mm in depth.

*Flower type.*—Rotate.

*Flower buds.*—Sterile flowers; an average of 7 mm in length and 4 mm in diameter, ovate in shape, 144A in color at base and upper portion 145B in color, fertile flowers; an average of 6 mm in length and 4 mm in diameter, broad obovate in shape, 144B in color at base, upper portion a blend of 70D and 157D.

*Peduncles.*—Primary peduncle; very strong, flattened oval in shape, an average of 2 cm in length and 2.5 mm in width, a blend of 144A and 138A in color, surface dull and sparsely covered with very minute pubescence and lenticels; an average of 4, 187A in color, an average of 3 mm in length and 1 mm in width, strong, secondary peduncles; strong, an average of 1 cm in length and 2 mm in width, sparsely covered with very minute pubescence, and lenticels similar to primary peduncle, 146B in color.

*Pedicels.*—Sterile flowers; held primarily at an average angle of 45° to upright from peduncle, an average of 1.5 cm in length and 1.5 mm in diameter, moderately strong strength, color; a blend of 68A and 68B in color, dull and very finely pubescent surface, fertile flowers; held at an average angle of 20° from vertical, an average of 2.5 mm in length and 1 mm in diameter, moderate strength, 138A in color, glabrous surface.

*Petals.*—Sterile flowers; an average of 4, rotate in arrangement but remain closed as a petal spot, acute-rounded apex, cuneate base, entire margins, elliptic and concave in shape, an average of 3 mm in length and 2 mm in width, both surfaces; glabrous and dull, color; upper and lower surfaces when opening 145B, upper and lower surfaces when fully opened 65B, color not fading, fertile flowers; an average of 5, rotate in arrangement, elliptic and concave in shape, entire margin, acute to rounded apex, cuneate-truncate base, an average of 4 mm in length and 2.5 mm in width, upper and lower surface glabrous and dull, color upper surface when opening and fully open; a N77B with thin margin of 155A, color lower surface when opening and fully open; a blend of N77B and 155A in color, shed quickly.

*Sepals.*—Sterile flowers; 4 to 5, rotate arrangement, overlapping, broadly acute apex with minute notch, broadly cuneate base, entire margins with occasional serrations, broadly ovate to rounded in shape and slightly wavy and concave in aspect, an average of 1.8 cm in length and 2.2 cm in width, both surfaces; glabrous and dull, color; upper and lower surfaces when opening 145C with apices and gradually the rest of the sepal becoming suffused with 60B and 60C with markings towards base and slight veins of 155A, upper surface when fully opened; a blend of 60A, 60B and 60C with rare markings of NN137A, lower surface when fully opened; a blend of 63B and 63C with veins 60C with rare markings of 137C and 137D, non-fading until browning. fertile flowers; an average of 5, elliptic in shape, entire margin, acute apex, 1.2 mm in length and width, and truncate base, both surfaces are glabrous and dull, color; upper and lower surface when opening and fully opened N77A, color not fading.

Reproductive organs:

*Presence.*—Observed on fertile flowers only, if present on sterile flowers, they are not exposed as petals remained closed.

*Stamens.*—An average of 8, anther; broad kidney-shaped, an average of 1.5 mm in length and 8D in color, filament; an average of 2.5 mm in length and 155A in color, pollen moderate to low in quantity and 177A in color.

*Pistils.*—1, 3-lobed, 2 mm in length and width, stigmas; club-shaped and 159C in color, styles; an average of 1.5 mm in length and 68D in color, ovary is 144B in color, triangular in shape, 3 mm in length and 3 mm in width at apex.

*Fruit and seed.*—None observed to date.

It is claimed:

1. A new and distinct cultivar of *Hydrangea* plant named 'Horthat' substantially as herein illustrated and described.

* * * * *